US00PP15533P3

(12) United States Plant Patent
de Groot

(10) Patent No.: US PP15,533 P3
(45) Date of Patent: Feb. 8, 2005

(54) HYBRID TEA ROSE PLANT NAMED 'PAND565'

(50) Latin Name: *Rosa hybrid*
Varietal Denomination: Pand565

(75) Inventor: Henk C. A. de Groot, De Kwakel (NL)

(73) Assignee: Panorama Roses N.V., Curacao (NL)

( * ) Notice: Subject to any disclaimer, the term of this patent is extended or adjusted under 35 U.S.C. 154(b) by 0 days.

(21) Appl. No.: 10/437,964

(22) Filed: May 13, 2003

(65) Prior Publication Data

US 2003/0221230 P1 Nov. 27, 2003

(51) Int. Cl.[7] ..... A01H 5/00

(52) U.S. Cl. ..... Plt./130

(58) Field of Search ..... Plt./130, 132

(56) References Cited

PUBLICATIONS

UPOV–ROM GTITM, Plant Variety Database, 2003/04 GTI Jouve Retrieval Software, Citation for Rosa 'Pand565'.*

* cited by examiner

*Primary Examiner*—Anne Marie Grunberg
*Assistant Examiner*—June Hwu
(74) *Attorney, Agent, or Firm*—Christie, Parker & Hale, LLP

(57) ABSTRACT

A new and distinct Hybrid Tea rose plant having attractive pink and white bicolor flowers.

1 Drawing Sheet

Classification: The present invention relates to a new *Rosa* hybrid plant, korcilmo×unknown.

Varietal denomination: The new plant has the varietal denomination 'Pand565'.

BACKGROUND OF THE INVENTION

The present invention relates to a new and distinct variety of rose plant of the Hybrid Tea rose class, which was created by crossing as seed parent the variety known as 'Korcilmo', U.S. Plant Pat. No. 8,580, and an unnamed, undistributed seedling as pollen parent.

SUMMARY OF THE INVENTION

Among the novel characteristics possessed by this new variety which distinguishes it from its parents and all other varieties of which I am aware are the pink flowers and the outer petals with a white surface and strong stems.

Asexual reproduction by propagation by grafting of the new variety as performed in De Kwakel, The Netherlands shows that the foregoing and other distinguishing characteristics come true to form and are established and transmitted through succeeding propagation.

COMPARISON WITH PARENTS

Among other respects, the new variety differs from its parents in flower color, inasmuch as the seed parent has pink flowers whereas the new variety has flowers that are pink inside and white outside.

BRIEF DESCRIPTION OF THE ILLUSTRATION

The accompanying illustration shows a typical specimen of the new variety depicted in color as nearly true as is reasonably possible to make the same in a color illustration of this character. In the illustration are seen a new shoot 1; leaflets 2, 3 and 4; a stem with thorns 5; flowers of different stages of development 6, 7, 8 and 9; and reproductive organs 10, 11 and 12.

DESCRIPTION OF THE NEW VARIETY

The following is a detailed description of the new variety with color terminology in accordance with The Royal Horticultural Society Colour Chart (R.H.S.C.C.). The terminology used in color description herein refers to plate numbers in the aforementioned color chart. Phenotypic expression may vary with light availability, environmental and cultural conditions.

The following observations are made of 9-month old plants grown in a greenhouse in De Kwakel, The Netherlands during January from a grafted cutting.

Flower:

*Blooming habit.*—Continuous.
*Bud.*—Size: About 5 cm long by about 3.5 cm wide.
*Form.*—Ovate.
*Color.*—Outside near 62B; inside near 67B.
*Sepals.*—Curly pointed apex, texture upper surface smooth, texture lower surface smooth.
*Size.*—Length about 3.5 cm; width at base 1 cm.
*Color.*—Top surface — Near 144A. Undersurface — Near 145A.
*Peduncle.*—Length: About 10 cm.
*Aspect.*—Smooth.
*Strength.*—Erect.
*Color.*—Near 143A.
*Bloom.*—Size: About 12 cm.
*Borne.*—Singly, one to a stem.
*Form.*—View from above is irregularly rounded; upper part of the flower is flattened convex; lower part of the flower is flat.
*Petalage.*—About 29.
*Color (⅓ to ½ open).*—Outer petals: Top Surface — Near 68A.
*Undersurface.*—Near 159D.

*Inner petals.*—Top Surface: Near 67C. Undersurface: Near 65A.
*Base of petals* (*point of attachment*).—Near 4C to 4D.
*General tonality from a distance.*—Pink.
*Color* (*fully opened*).—Outer petals: Top surface — Near 68A. Undersurface — Near 159D.
*Inner petals.*—Top Surface — Near 67C. Undersurface — Near 4C to 4D.
*Base of petals* (*point of attachment*).—Near 65A.
*General tonality from a distance.*—Pink.
*Color change.*—Color does not change as bloom ages.
*General tonality from a distance.*—Pink.
*Petals.*—Texture: Thick.
*Appearance.*—Inside — Velvety. Outside — Satiny.
*Form.*—Nearly round; width about 5.5 cm; height 6 cm; strong reflexing of the margin.
*Arrangement.*—Imbricated.
*Petaloids in center.*—Few, about 2 to 4, obovate shape, size 10 to 12 mm width, 35 to 45 mm length, color upper surface near 68C, color lower surface near 4D.
*Persistance.*—Persistent.
*Fragrance.*—Slight.
*Lasting quality.*—On the plant: About 14 days.
*In the vase.*—About 9 days.

Reproductive organs:
*Stamens, filaments and anthers Arrangement.*—Regularly arranged around styles.
*Filaments.*—Average length 8 to 11 mm, color near 38A.
*Anthers.*—Average size 1 to 2 mm, color near 22C.
*Pollen.*—Near 161C.
*Styles.*—Average length about 6 to 8 mm, color of pistil near 4D.
*Stigmas.*—Near 45A.
*Hips.*—Hips and seeds have not been observed because the plant has never grown to the stage of seed development and because the variety is grown for producing floral stems.

Plant:
*Form.*—Upright.
*Growth.*—Vigorous uniform branching.
*Height attained* (*first season*).—About 180 cm, width about 60 to 70 cm.
*Foliage.*—Compound 3, 5 and 7 leaflet leaves, pointed, base shape round.
*Size.*—Length about 9 cm; width about 8 cm.
*Quantity.*—About 12 leaves per stem.
*Leaflet apex.*—Broad.
*Color.*—New foliage: Upper side — Near 187C. Underside — Near 183C.
*Mature foliage.*—Upper side — Near 137A. Underside — Near 137C.
*Shape.*—Broad oval.
*Texture.*—Upper side — Medium glossy with deep lying veins. Underside — Matte.
*Edge.*—Serrated.
*Serration.*—Serrate.
*Petiole.*—Texture smooth.
*Top surface.*—Near 187B.
*Underside.*—Near 191A.
*Stipules.*—Short, length about 0.5 cm; color near 137C, texture upper surface and lower surface are smooth.
*Auricle.*—Not present.
*Rachis.*—Smooth; 3 to 4 prickles.
*Wood.*—New shoots: Color: Near 177A and 147B to near 138A.
*Bark.*—Smooth.
*Old wood.*—Color: Near 137B and 147B to near 195B.
*Bark.*—Smooth.
*Flower stem length* (*from last cut*).—About 70 to 100 cm.
*Thorns.*—Quantity: Few on lower part; 3 to 4 between nodes; top (⅓) no prickles; few on laterals from basal canes.
*Form.*—Deep concave.
*Length.*—Length about 1 cm; base width about 0.5 cm.
*Color* (*when young*).—Near 174B.
*Color* (*when mature*).—Near 181A.
*Position.*—Irregular.
*Prickles.*—None.

I claim:

1. A new and distinct Hybrid Tea rose plant of the variety substantially as shown and described.

* * * * *

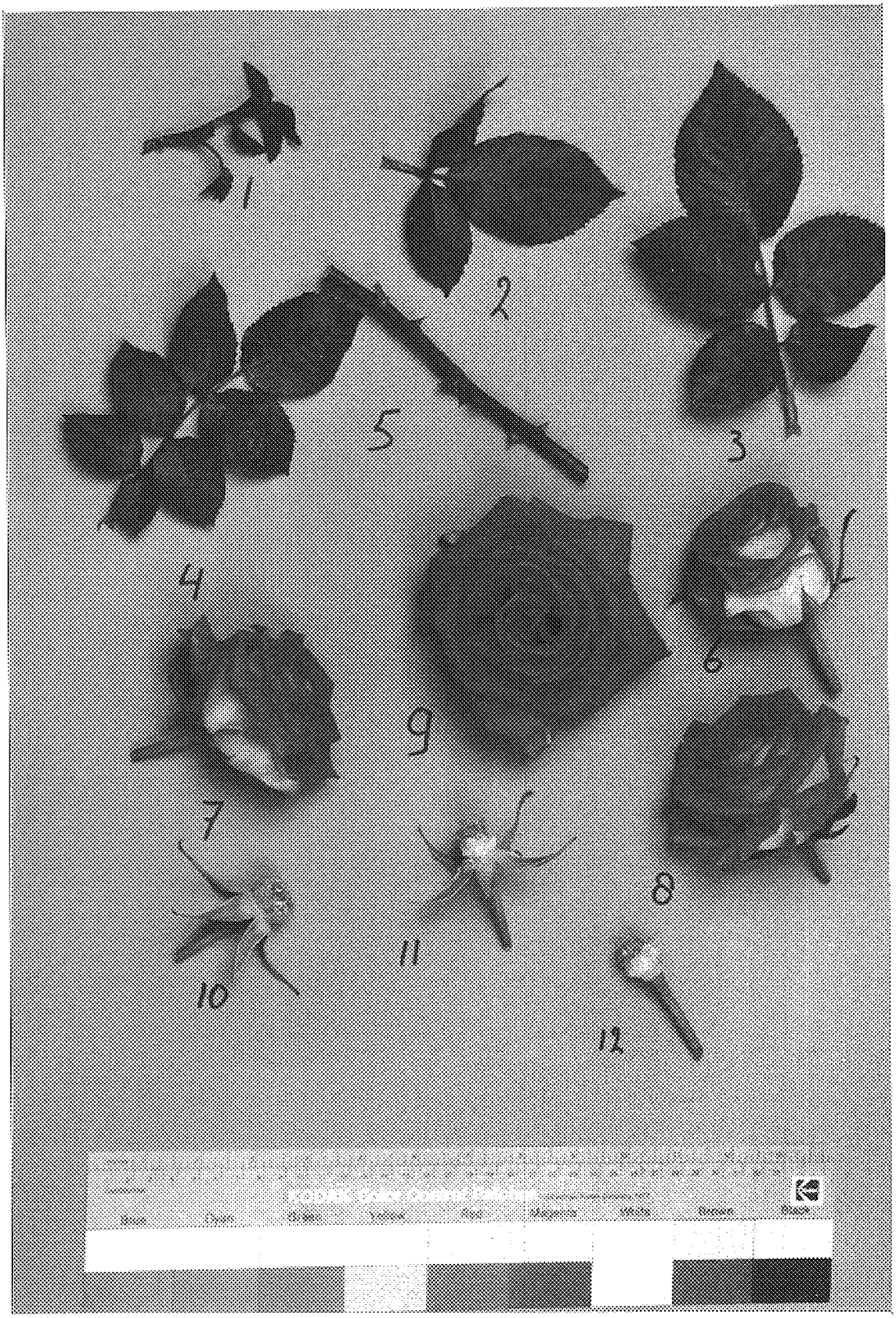
1
2
3
4
5
6
7
8
9
10
11
12